United States Patent [19]
Corvi-Mora

[11] Patent Number: 4,639,469
[45] Date of Patent: Jan. 27, 1987

[54] METHOD OF PREPARING SOBREROL AND THE PHARMACEUTICAL APPLICATION OF THE SOBREROL THUS OBTAINED

[76] Inventor: Camillo Corvi-Mora, Via Spiga, 42, Milan, Italy

[21] Appl. No.: 429,445

[22] Filed: Sep. 30, 1982

Related U.S. Application Data

[63] Continuation of Ser. No. 198,269, Oct. 17, 1980, abandoned, which is a continuation of Ser. No. 13,414, Feb. 21, 1979, abandoned, which is a continuation of Ser. No. 622,415, Oct. 14, 1975, abandoned, which is a continuation of Ser. No. 94,188, Dec. 1, 1970, abandoned.

[30] Foreign Application Priority Data

Apr. 17, 1970 [IT] Italy .............................. 23490 A/70

[51] Int. Cl.⁴ .......................................... A61K 31/045
[52] U.S. Cl. ..................................................... 514/729
[58] Field of Search ........................................ 424/331

[56] References Cited

U.S. PATENT DOCUMENTS 2,815,378 12/1957 Klein .............................. 424/343 X
2,949,489 8/1960 Durbetaki et al. ................. 424/343
3,592,908 7/1971 Corvi-Mora ....................... 424/278

OTHER PUBLICATIONS

Schmidt—*Chemische Berichte*, Jahrg. 86, No. 11, (1953), 1437–1444.

Primary Examiner—Frederick E. Waddell
Attorney, Agent, or Firm—Ostrolenk, Faber, Gerb & Soffen

[57] ABSTRACT

The use of highly pure sobrerol-d,1 as a balsamic and a respiratory analeptic.

5 Claims, No Drawings

METHOD OF PREPARING SOBREROL AND THE PHARMACEUTICAL APPLICATION OF THE SOBREROL THUS OBTAINED

This is a continuation of application Ser. No. 198,269, filed Oct. 17, 1980, which is a continuation of application Ser. No. 13,414, filed on Feb. 21, 1979, which is a continuation of application Ser. No. 622,415 filed on Oct. 14, 1975, which is a continuation of Ser. No. 94,188, filed Dec. 1, 1970, all abandoned.

This invention relates to the pharmaceutical use of highly pure sobrerol d,l as a balsamic and respiratory analeptic composition and to such compositions containing this compound.

Sobrerol, which has been known since 1797, and was isolated in the pure state as early as 1851, by Sobrero, from whom it gets its name, is the chemical product 1-methyl-4α-hydroxyisopropylcyclohexenol-6; i-1-p-menthene-6,8-diol, also known as pinol hydrate or pinene oxide-hydrate, in its racemic (d,l) form and in its optically active form, as also in all the possible stereoforms (cis-trans).
M.W. 170
melting point 150° C. in the active forms
and melting points 130°–131.5° C. in the d,l form

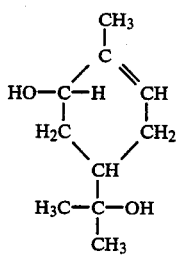

Sobrerol has been the object of much research, however, as far as it is known, it has never been produced on an industrial scale.

Prior uses of sobrerol include its use as an intermediate compound in the preparation of optically active carvones, carveols, etc., and their derivatives, designed for use in the perfume, flavor, cosmetic industries and the like. To this end, the processes for its preparation were aimed at obtaining optically active compounds which have a higher melting point of 150° C. and lower solubility, and avoid the formation of the racemic compound which has a melting point around 130° C. and is relatively soluble.

These methods have never gone beyond the laboratory stage, gave insufficiently high yields and in general, in order to produce a pure product, required laborious purifying operations. It was therefore necessary to devise an economical industrial process for the production of a sufficiently pure sobrerol.

The process in accordance with the present invention fills this requirement for the preparation of sobrerol-d,l on an industrial scale with a high degree of purity (98%) and high stability, good yield (80%) using conventional, readily available apparatus.

In the course of the studies which led to the development of the present process of making sobrerol-d,l it was discovered surprisingly that very pure sobrerol-d,l obtained by this process has important therapeutic properties as a balsamic agent (fluidifier and expectorant) and as a respiratory analeptic. These properties can be utilized with maximum efficiency due to the sufficient solubility which this form of sobrerol exhibits, as compared with the optically active sobrerols.

The therapeutic activity and significance of sobrerol-d,l has been confirmed by numerous experiments which have pointed up the chemicalpharmacotoxycological and clinical characteristics of sobrerol-d,l prepared in accordance with the method of the present invention.

The particular suitability of the sobrerol-d,l obtained in accordance with the present invention for application in the therapeutic field, is strictly related to obtaining a high-purity product, i.e. one free of aldehyde and ketone impurities which are quite often present in the products of oxidation of the α-pinene obtained from turpentine oil. These impurity products can be highly toxic and they can adversely affect the pharmacological activity of sobrerol.

An object of the invention is to produce a sobrerol-d,l suitable for therapeutic applications, in particular as a balsamic and respiratory analeptic, having a very low toxicity ($LD_{50}$500 mg/kg on mice).

Another object of the invention is to produce pharmaceutical compositions which contain pure sobrerol-d,l combined with other pharmacologically active products and with conventional excipients etc. used customarily in the pharmaceutical art for the various pharmaceutical compositions.

Other objects, characteristics and advantages of the process and the products of the invention and of their application to therapeutic purposes, will become apparent to one skilled in this art from the present description, the examples and the reports of clinical tests described below.

As already pointed out, the production of sobrerol is not of itself novel. The oxidation of α-pinene, contained in the turpentine oil, which is substantially the starting material, has been described in many theoretical works and in industrial patents, as already cited. Various agents have been proposed for epoxidation, such as oxygen, peracetic acid (Arbusow and Michailow—J. Prackt. Chem 127,1 (1930), parphthalic acid (Lombard and Heywang—Soc. Chim, France 1954, 1214), various percarboxylic acids in the presence of neutralisers (British Pat. No. 877,632 date Sept. 20, 1961); in addition, perbenzoic acid in a chloroform solution is also mentioned (at 0° C. with a 72.36% theoretical yield) in U.S. Pat. Nos. 2,815,378 and 2,949,489 it should be noted that all the above describe small scale production processes.

Oxidation of α-pinene, as hereinbefore described produces mixtures in which 2,3 epoxypinene (α-pinene epoxide) predominates, which can be considered as the precursor of sobrerol. Afterwards, the epoxide is hydrated to sobrerol with water, generally in a slightly acid environment but, too, in some cases, in a neutral or slightly alkaline environment when the aim is to produce optically active sobrerol from α-pinene having a similar optical activity. Thus, in U.S. Pat. No. 2,815,378 the pinene epoxide, obtained by oxidation of perbenzoic acid, is hydrated with water in neutral or slightly alkaline pH conditions to avoid the production of the racemic form. In U.S. Pat. No. 2,815,378 the process of isolating sobrerol is laborious and it is difficult to obtain a pure product.

In U.S. Pat. No. 2,949,489, which claims a 100% yield, the hydration of α-pinene oxide (obtained in a known manner by the oxidation of α-pinene using perbenzoic acid) with water and catalytic quantities of $CO_2$, is described; operational conditions: weight ratio:

1 to 50 parts of α-pinene oxide per 100 parts of aqueous solution; 0.1 to 0.2 g of $CO_2$ per 100 g of $H_2O$; 5 mins-1 hour; pH around 3.8+6.9; temperature: 0°+35° C.).

Accurate tests I have made of the procedure set forth in U.S. Pat. No. 2,949,489 have repeatedly produced yields no higher than 50%. It might be supposed, therefore, that the analytical methods described there are inadequate to provide a reliable quantitative assessment of the product obtained. In fact, IR analysis by superimposition on the spectrum of a product obtained by the Pope method (1832), referred to above can only be of a qualitative character and does not provide evidence as well as for the chemical analysis data referred to in Table I. In addition the following has been observed: (a) the final drying at 120° F., described for the end product of example 1, causes complications since the sobrerol, when heated in a stove at 120° F. sublimates and even minimal traces of foreign substances of an acidic nature are capable of altering it; (b) the crystalline sobrerol, obtained at low temperature as described in said reference, incorporates oily substances which can only be eliminated by careful rinsing which is not referred to in the Patent.

In fact, my repeated tests have confirmed that the product obtained in accordance with said Patent is contaminated by adhering oil and the effective yield, after washing with light petroleum fractions, is no higher than about 50% of the theoretical yield. This was determined by gaschromatographical analyses.

Compared with the various prior art processes cited above, the process of the present invention achieves a substantial advance in the art since it provides a high-purity product in a high yield. This product is obtained from α-pinene by a two-stage operation.

In the first stage, the epoxidation of α-pinene using perbenzoic acid, is characterized by the treatment of the α-pinene (95% according to gas chromatographic analysis), with a specific concentrated oxidising solution of perbenzoic acid in methylene chloride, preferably in chloroform, and more preferably with a special 15 to 30%, preferably 18 to 21% solution of perbenzoic acid in chloroform, at a temperature ranging between −1° C. and −6° C. for a relatively short period of between 4 and 8 hours, usually 5-6 hours For the preparation of this chloroform solution of perbenzoic acid, the procedure described on a laboratory scale by Y. Ogata and Y. Sawaki (Tetrahedron Vol. 30 pages 3327–3332 1967), was followed, suitably modified for use on an industrial scale basis in accordance with another feature of the present invention in that, in extracting the perbenzoic acid from the slightly acidic, sulphuric acid solution, the precise quantity of chloroform required to obtain said concentration provided for the oxidation of the α-pinene, is used, this will be illustrated by example I which follows. By carrying out epoxidation in this way, very high yields, of between 80 and 90% of pinene epoxide, are obtained, a titer of 97 to 98% being obtained after the purification described in example I.

A comparison of analogous known methods (which are operated on average at temperatures of 0° C. or more, with perbenzoic acid concentrations of between 8 and 10% and reaction times of 24 hours and more), clearly shows the superiority of the present process in which the use of high concentrations of perbenzoic acid allows a substantial reduction in the reaction volume and thus in the overall size of the machinery in which the process is carried out, a reduction in the quantity of chloroform required and thus a reduction in the time required for eliminating the chloroform. It will be observed that the reaction time is virtually halved (8-12 hours instead of 24 hours or more) while a constant epoxide yield of between 80 and 90% of the theoretical is obtained, compared with the substantially lower yields of the earlier processes the yield calculations for which are based upon the recovery of part of the α-pinene which has not reacted and which is recycled.

In the second stage of the process of the present invention, the pinene epoxide is subjected to hydration in an aqueous solution of $CO_2$ at around 36° to 100° C., the ratio of α-pinene oxide to aqueous solution of $CO_2$, being around 55 to 100 parts by weight of α-pinene oxide per 100 parts by weight of said solution; under such conditions, the pH 3.5-3.9 of the aqueous $CO_2$ solution is clearly acidic in order to cause the formation of racemic sobrerol.

The sobrerol-d,l obtained is then purified by washing and dried in a vacuum stove at a pressure below atmospheric pressure at a relatively low temperature, for example 30° C.; under conditions that avoid sublimation of the product; drying at normal pressure and an elevated temperature, for example at 120° C., as provided for in U.S. Pat. No. 2,949,489, may alter the final product (for example, to convert it to pinol) and result in a loss on sobrerol through partial sublimation.

This process makes it possible for the first time to achieve the production of pinene epoxide and sobrerol on an industrial scale, offering at the same time substantial advantages such as minimal overall dimension and hence optimum plant output, minimum risk of decomposition of the perbenzoic acid due to the low reaction temperature, exceptionally high yields (80%) and a high purity (98%) sobrerol-d,l.

For a better understanding of the foregoing, there now follows a number of examples of the process in accordance with the present invention, which examples are intended purely as an illustration and in no way limit the scope of the invention.

EXAMPLE I

Preparation of the epoxidizing reagent

Perbenzoic acid in a chloroform solution—In a stainless steel reaction vessel of 1500 l effective capacity equipped with agitators and external water cooling, there are placed 280 l of water to which 2.5 kg of $MgSO_4.7H_2O$ and 30 kg of caustic soda (NaOH) are added. The temperature of the solution obtained is between 15°-20° C. Thereafter, 75 l of hydrogen perioxide ($H_2O_2$), 120 vol., and 375 l of methyl alcohol ($CH_3OH$), are introduced maintaining the temperature at about 15°-20° C. Then, very rapidly, 60.5 kg of 100% benzoyl peroxide are added. After stirring for ¼ hour, the solution obtained is discharged into a reactor-separator having a capacity of 2000 l, equipped with agitators and external cooling, in which there have previously been prepared 750 l of 20% sulphuric acid. Addition takes place very rapidly and the temperature is maintained at 15°-20° C. At the completion of the addition operation, the solution is extracted using 200 l of chloroform, in one operation only, and allowed to separate. In this way, around 250 l of a chloroform solution of perbenzoic acid are obtained, at a concentration of around 22 to 23%. The yield is 80% of the theoretical (around 55 kg of perbenzoic acid).

Before using the chloroform solution thus obtained, for epoxidizing, the same is dried using anhydrous sodium sulphate in a vessel cooled to 0° C.; it is then filtered through a cooled filter and diluted to the desired concentration by the addition of chloroform.

EXAMPLE II

Preparation of α-pinene epoxide (a) 725 ml of 20% chloroform solution (145 g) of 100% perbenzoic acid, are loaded into a glass 2 l-reactor vessel externally cooled to −15° C. Over a period of around 2 hours, 145 g of 95% α-pinene are dripped in maintaining the temperature between −1° C. and −6° C. and stirring. Stirring is continued for 1 hour, cooling down to −10° C. to complete the reaction. Benzoic acid is precipitated out in the reaction and is eliminated by washing the chloroform solution with a 20% solution of sodium carbonate. The excess sodium carbonate is extracted in a subsequent washing operation with water. The chloroform solution which contains the α-pinene epoxide is rendered anhydrous by treating it with anhydrous sodium sulphate or with anhydrous calcium chloride. The now anhydrous solution is distilled under a vacuum of 70/100 mm until the chloroform is completely eliminated. The raw product thus obtained distilled under vacuum in a suitable rectification column in order to obtain a product which, according to gaschromatographical analysis, has a titer of 97–98%. The product is collected at 4 mm of pressure at a temperature of 39° C. and at 8 mm at a temperature of 47° C.

(b) 550 ml of a 23.3% (151 g) chloroform solution of 100% perbenzoic acid, are loaded into a glass reactor vessel of 2 l capacity, externally cooled to −15° C. Over a period of around 2 hours 150 g of 95% α-pinene are dripped in, maintaining the temperature between −5° C. and −2° C. The solution is then stirred for 1 hour, lowering the temperature to −10° C. At this temperature the perbenzoic acid which has precipitated out is filtered off. The chloroform solution obtained is washed with a small quantity of a 20% alkaline solution of sodium carbonate ($Ha_2CO_3$), in order to eliminate the contained residual benzoic acid. The process is then completed as in example 2a.

EXAMPLE III

Production of α-pinene epoxide on an industrial scale

In an effective 800 l glass lined reactor vessel, equipped with stirrers and externally cooled to −15° C., 107.5 kg of perbenzoic acid in the form of a 20% solution in chloroform are loaded. External cooling is carried out in order to bring the internal temperature to −5° C. Over a period of around 4 hours 108.8 kg of 95% α-pinene are dripped in. This addition phase completed, stirring is continued for 1 hour. The chloroform solution obtained is washed with 220 l of a 20% solution of sodium carbonate and then with 200 l of water. Drying is then carried out with 5% (p/v) of anhydrous sodium sulphate.

135 kg of raw product, equal to 93 kg of α-pinene epoxide, are obtained. The yield is 82% of the theoretical.

The anhydrous solution, after filtering off the sodium sulphate, is rectified under vacuum.

EXAMPLE IV

Preparation of sobrerol-d,l (a) 500 g of α-pinene oxide are dispersed in 500 ml of water which has been processed at 22° with $CO_2$, to a pH value of 3.5. The temperature which is initially 35° C., rises rapidly to 100° C.; sobrerol-d,l then commences to separate out in the form of white crystals. The reaction mass is externally cooled to bring the temperature to 15° C. The product is collected, centrifugated and washed with a small quantity of petroleum ether. The yield corresponds to 500 g of sobrerol-d,l.

(b) 515 g of α-pinene oxide are dispersed in 1000 ml of water into which $CO_2$ is bubbled to a pH value of 3.9. The temperature, initially 36° C., rises rapidly to 72° C.

The sobrerol-d,l is separated off and collected as described in Example I. Yield: 520 g of sobrerol-d,l.

EXAMPLE V

Preparation of sobrerol on an industrial scale

In a stainless steel reactor vessel equipped with stirrers and external cooling, and with an effective capacity of 100 l, 50 l of deionized water are loaded and carbon anhydride is bubbled through until a pH value of 3.5 is reached. At a temperature of 36° C. α-pinene oxide is rapidly introduced (50 kg). The temperature rises to 95° C. The sobrerol then separates out in the form of a white crystalline mass. At this point, the product is externally cooled to 15° C. and separated by centrifugation. The motherlyes are clear. There are small quantities of an oily phase in the crystalling product which are removed using small quantities of petroleum ether. The centrifuged product is dried in a vacuum stove at 30° C. for 12 hours. The process yield is higher than 80% of the theoretical yield of pure sobrerol-d,l.

As already stated, the sobrerol-d,l so obtained is particularly suitable for balsamic therapy of respiratory diseases.

Preparations having as an active base oxidation products of turpentine oil or other terpene oils (pine oil, nialuli oil, eucalyptus oil) have been known and commercially available for a long time; these oils are almost insoluble in water and generally used in the form of suppositories or aqueous phials, with the addition of surface active agents for hydrodispersion. These contain admixed substances having a balsamic action, substances for fluidifying phlegm and substances having a stimulative effect on the respiratory center, plus at the same time substances having an irritant effect (aldehydes) or substances which will produce intolerance phenomena or unpleasant side effects, such as hydrocarbons, in particular pinenes. In addition, their insolubility in water requires—in the parenterally administration—the use of special solvents or oily vehicles or, in aqueous phials, surface-active dispersing agents. Despite this, their injectability leaves a great deal to be desired.

The novel sobrerol-d,l prepared in accordance with the process of the present invention, represents an improvement from the technical, therapeutic and economic points of view. Its solubility in water, in particular, is superior to all the balsamic terpene products (3.3 g/100 ml of water at 15° C. compared with 0.2 for eucalyptus and 0.04 for menthol, as well as virtually complete insolubility in the cases of α-, β-pinene bornile acetate and others) and is in any case sufficient to allow the preparation of aqueous phials in therapeutic doses, without using surface-active agents.

In addition, the pharmacotoxicological researches regarding sorbrerol-d,l synthesized by the process of the present invention, have yielded very favorable results as far as toxicity and tolerance are concerned, with the possibility of intravenous administration. Cardiographic and pneumographic tests have also confirmed favorable results.

As regards the toxicity, the tests of acute toxicity on albino rats (Wistar adults, male sex) and on albino mice (Swiss, adults, male sex) according to the suggested Lichtfield and Wilcoxon system have proved an $LD_{50}$ value of 580 mg/kg i.v. (with fiducial limits 436–77) (P=0.05) (S=1.34).

The dose corresponds to approximate 580 times the single dose pro-Kg injectable in human therapy, such as set out hereinafter, namely about 1 mg/pro-Kg Tests comprising the daily prolonged administration in the rat, for 90 and 150 days, in doses up to about 370 times the single dose foreseen in human therapy, gave quite satisfactory results as regards the tolerability of the sobrerol-d,l.

Analogous positive statement about the tolerability of the sobrerol-d,l was deduced from the tests, conducted for the assessment of possible negative effects on the reproductive process (fertility, gestation, embryology, fetal development): the results of the related experiment permit the exclusion of every interference of the sobrerol with the reproduction process.

It was shown in the functional tests that the sobrerol-d,l causes an increase of amplitude and frequency of breathing in the treated animals, and acts as an antagonist of the depressive action of morphine, exerting an analeptic respiratory action. No alterations were noticed in the electrocardiographical parameters examined.

The clinical experiments were carried out on man (adult, or child) with the following indications:

Acute or chronic diseases of the respiratory apparatus with increased excretion, acute and chronic bronchitis, bronchioctasis, bronchopneumonia, particularly if associated with respiratory insufficiency (asthma and emphysema) rhinopharyngitis and laryngotracheitis. Pre- and post-operative treatments of the respiratory tract.

The product in aerosol form was also successfully experimented in the sterhinalaryngological field.

The effect of the sobrerol-d,l was estimated by means of an agile clinical system, as can be obtained with a "sequential trial", bringing into effect the search in subjects affected with chronic bronchitis, sometimes in the phase in which the disease becomes more serious yet again, also concomitant with ether unhealthy affections.

Pairs of comparable patients have chosen: one of the patients was treated with sobrerol-d,l, a phial i.m. in the morning and a suppository in the evening; on the contrary, no balsamic therapy was administered to the other patient, as a comparison.

It was necessary to associate an antibiotic treatment for some pairs. The subjects who were to form the pairs, were selected with particular care (the pairs were formed with patients present in the clinic in the same period or in periods fairly close to each other) se that they would be as clinically comparable as possible, especially as regards the quantity and characters of the expectoration (purulent means).

We hold, in fact, that the most important element in the evaluation of the effectiveness of a balsamic product is just given by the changes in the amount of the expectoration during the 24 hours, instead other clinical elements, such as the objective tnoracic report, coughing, dyspnea, are very difficult elements to value quantitatively, as well as being subjected to extra-therapeutic influences which can alter the real value.

We have, however, considered as critical in the valuation of the clinical results, the halving time of the amount of expectoration (of the 24 hours) determined at the beginning of the observation period, while instead, only a relative value was given to the other clinical signs.

Some examples of numerous case histories taken from extensive clinical-therapeutical tests, to which the sobrerol-d,l according to the present invention was subjected, are hereinafter tabulated as confirmation of the exceptional balsamic and respiratory analeptic activity.

The tests refer to adult subjects (Table I) and to children (Table II).

The related cases only represent a few illustrative examples of a wide range of experiments, which has confirmed the optimum tolerability of sobrerol-d,l-based pharmaceuticals, which, among other things, both in aequeous phials and in suppository form, are always agreeable to the patients.

In Table I, the dosage units in the phials consisted of:
60 mg in 3 ml
and the dosage units in the suppositories consisted of:
200 mg In the Table II, the dosage units in the phials B consisted of: 30 mg
and the dosage units in the suppositories B and L consisted of:
Supp. B=100 mg
Supp. L=20 mg

TABLE I

| No. | Name | Clinical card nos. | Sex | Age years | No. of days treatment | Results | Tolerance |
|---|---|---|---|---|---|---|---|
| 1 | P. O. | 212 | M | 55 | 8 | Regression in the symptomatology, reduction in expectoration and coughing | Optimum |
| 2 | S. B. | 311 | F | 53 | 12 | Reduction in expectoration, general medical improvement. | Optimum |
| 3 | C. A. | 280 | F | 62 | 11 | Regression in the symptomatology, reduction in coughing, in dyspnea, and in expectoration | Optimum |
| 4 | B. E. | 432 | M | 73 | 11 | Reduction in expectoration, general medical improvement. | Optimum |
| 5 | B. A. | 281/65 | M | 77 | 30 | Reduction in dyspnea and expectoration. | Optimum |
| 6 | B. En. | 334/65 | M | 59 | 60 | Reduction in and fluidification of phlegm, reduction in coughing | Optimum |
| 7 | B. S. | 136/65 | M | 52 | 20 | Reduction in dyspnea and in coughing | Optimum |

TABLE I-continued

| No. | Name | Clinical card nos. | Sex | Age years | No. of days treatment | Results | Tolerance |
|---|---|---|---|---|---|---|---|
| 8 | P. C. | 256/65 | M | 63 | 30 | Reduction in dyspnea, in expectoration and in coughing | Optimum |

NOTE:
The diagnoses on Subjects 1 to 4 refer to cases of chronic bronchitis with respiratory deficiencies: The diagnoses on Subjects 5 to 8 refer to cases of ulcero-fibrositic tuberculosis. The pro-dio therapy was 1 phial plus 1 suppository in all cases.

TABLE II

The sobrerol-based pharmaceutical compositions at doses reduced to ½ and 1/10 of the adult dose, have also been employed in pediatric applications. We give here a Table of some of the many cases treated with phials B and suppositories B (dose ½) and suppositories L (dose 1/10).

| No. | Name | Clinical card Nos | Sex | Age months (m) years (a) | Phials B/ Supp. B Supp. L/day | Days of treatment. | Diagnoses. | Results X-ray before | X-ray after |
|---|---|---|---|---|---|---|---|---|---|
| 1 | B. F. | 962 | M | 12 m | Phial B = 1 | 7 | Bronchiolitis | Accentuated trauma. | Normal |
| 2 | E. C. | 1152 | F | 10 m | Supp. L = 2 | 8 | Bronchitis | Accentuated trauma. | " |
| 3 | C. H. | 1158 | F | 4 m | Supp. L = 2 | 9 | Bronco-pneumonia | Congestion base dx. | " |
| 4 | S. C. | 1140 | M | 5 a | Supp. B = 2 | 9 | Bronchitis | Accentuated trauma. | " |
| 5 | F. C. | 1346 | F | 7 a | Phial B = 1 | 5 | Bronchitis | Accentuated trauma. | " |

NOTE:
In all cases 1 to 5, a treatment associated with antibiotics was employed. The tolerance in the pediatric experiments was optimum throughout, even with very young children.

Cases of pulmonary tuberculosis, silicosis, acute and chronic bronochitis in which there was a remarkable catarrhal component, bronchial asthma, emphysema, bronchiostasies were treated with the highest results. In the course of the experiment, subjective variations of the cough and expecteration symptoms and of objective thoracic alterations followed. Alterations in the dyspnea symptom and variations in the spiregraphic indices were also observed. The sobrerol-d,l has shown a very good therapeutic effect in the sense of a constant diminution in the cough symptom, while in the most cases the expectoration is reduced and also seems more fluid. The respiratory indicees, and particularly the vital capacity (V.C.) and the maximum breathing capacity/minute caused the recording of positive variations and further an evident increase in volume/minute of the MEVS ratio (maximum expiratory volume/second) VC and of the oxygen consumption/minute.

The above modifications are attributed both to the reduction of the expectoration and to its increased fluidity and to the respiratory analeptic effect of the composition.

The section of the sobrerol-d,l on the breathing was further evalued clinically, controlling the changes of some spirometrical indices after parenteral administration of sobrerol-d,l, on a group of patients with respiratory insufficiency resulting from chronic bronchitis. An increase of basal respiratory capacity (ventilation/minute) a tendency towards a greater impulse of the dynamic, maximum, pulmonary volumes (MV/m) is observed, while, as regards the static pulmonary volumes, there is an improvement in the vital capacity (VC) of the maximum respiratory capacity per second (MEVS) and of the Tiffeneau index, possibly for a bronchodilatory effect. As an indication of the balsamic activity of the sobrerol-d,l, its effect on the expectoration was considered, measuring the halving time of the amount of expectoration (of the 24 hours).

The balsamic activity of the sobrerol-d,l was convincingly confirmed; in fact, the amount of expectoration is generally reduced more quickly and clearly as compared to those patients not treated, while an improvement of the objective thoraci report is parallely observed.

In the course of clinical experiments undesirable, collateral phenomena or intolerance phenomena were not observed.

From the above it will be clear that the sobrerol-d,l in accordance with the present invention makes an unforeseen and essential contribution to balsamic theory, due to its outstanding characteristics of highpurity and consequent stability and possibility of accurate dosing; its negligible toxicity, water solubility sufficient for well tolerated administration in aqueous phials, without intevention of surface-active agents; and of its efficient balsamic effect, together with a stimulating action on breathing without undesired side-effects.

In practical therapeutics, sobrerol-d,l furthermore permits a useful association with numerous other pharmaceutical products such as antipyretics (for example acetaminophenol, acetylsalicylic acid, pyramidone), respiratory analeptics (metaraminol, 3-ethoxy-4-hydroxy benzoic diethylamide (Anacardiol), nicotinic diethylamide), antitussives (1-phenyl-4-chlorophenyl-3-dimethylaminopropane (1)-ol, hydrochloride (Clofedianol), sodium 2,6-di-terbutyl naphthalene sulphonate, dextrometherpham hydrobromide), antibiotics (tetracyaline hydrochloride, penicillin, streptomycin), broncho-dilatatories (isopreteral bitartrate,$\alpha$(3,4-dioxyphenyl)-$\beta$[2(3,4-methylene dioxyphenyl isopropyl amine]ethanol, 2-amino-1-phenyl-1-propanol hydrochloride).

Of course, the above listed cases are in no way limitative of the invention.

The pharmaceutical compositions comprising the above combinations with other active pharmaceuticals, can be mixed at the same time with conventional additives, excipients and the like, and processed in a conventional way to give granules, tablets, capsules, suppositories, syrups and for injection from phials solutions, etc.

Examples of pharmaceutical preparations, which are designed to illustrate the various possibilities of combination and forms of presentation of the sobrerol-d,l, in accordance with the invention, follow, although these examples are in no way limitative of the invention.

EXAMPLE VI

Antipyretic Combinations

| (1) tablets | Sobrerol-d,1 | 100 g |
|---|---|---|
| | Acetaminophenol | 200 g |
| | Maize starch | 105 g |
| | Lactose | 72 g |
| | Mg stearate | 3 g |

Granulation is carried out using 10% starch paste; the granulate dried at 50° C. The mixture is converted into tablets each weighing 0.480 g. and containing 100 mg of sobrerol and 200 mg of acetaminophenol.

| (2) capsules | Sobrerol-d,1 | 100 g |
|---|---|---|
| | Acetaminophenol | 200 g |
| | Maize starch | 103 g |
| | Lactose | 72 g |
| | Mg Stearate | 3 g |

The mixture is placed in sealed capsules. Each capsule contains 0.480 g of mixture corresponding to 100 g of sobrerol and 200 g of acetaminophenol.

| (3) Syrups | Sobrerol-d,1 | 8 g |
|---|---|---|
| | Acetaminophenol | 12.8 g |
| | Sugar | 400 g |
| | Sodium benzoate | 3 g |
| | Flavour | 5 g |
| | Caramel | 5 g |
| | Distilled water to make up to 1000 ml | |

The solution, obtained by dissolving the ingredients in distilled water at 60° C., is made up after cooling to a volume of 1000 ml and then filtered. Each ml of syrup contains 8 mg of sobrerol and 12.8 mg of acetaminophenol.

| (4) Suppositories | Sobrerol-d,1 | 200 g |
|---|---|---|
| | Acetaminophenol | 500 g |
| | Glycerides of saturated fatty acids made up to 2500 g | |

The constituents are melted at 40° C. and the melted mixture is poured into suitable containers. Each suppository, weighing 2.5 g, contains 200 mg of sobrerol and 500 mg of acetaminophenol.

EXAMPLE VII

Analeptic Compositions

| (1) Phiales | Sobrerol-d,1 | 60 g |
|---|---|---|
| | Anacardiol | 30 g |
| | Glucose | 150 g |
| | Double distilled water to make up to 3000 ml | | the solution obtained by dissolving the ingredients in double distilled water at 60° C., is made up to a volume of 3000 ml after cooling, and filtered. It is then portioned into 3 ml-phials which are sterilized at 120° C. for ½ hour. Each phial contains 60 mg of sobrerol and 30 mg of anacardiol.

| (2) Lupps: | Sobrerol-d,1 | 40 g |
|---|---|---|
| | Anacardiol | 23 g |
| | Ethanol | 308 g |
| | Flavour | 10 g |
| | Double distilled water to make up to 1000 ml. | |

The ingredients are dissolved in alcohol at 30° and the volume made up with distilled water. The filtered solution contains 40 mg of sobrerol and 25 mg of anacardiol, per ml.

EXAMPLE VIII

Antitussin Compositions

| (1) | Sobrerol-d,1 | 16 g |
|---|---|---|
| | Olefedianol | 4 g |
| | Sugar | 500 g |
| | Sodium benzoate | 3 g |
| | Flavour | 5 g |
| | Distilled water to make up to 1000 ml | |

The ingredients are dissolved in distilled water at 60° C. The cooled solution is filtered and made up to volume. Each ml of the syrup contains 16 mg of sobrerol and 4 mg of elefediemol.

EXAMPLE IX

Antibiotic Compositions

| (1) | Sobrerol-d,1 | 100 g |
|---|---|---|
| | Tetracycline HCl. | 250 g |
| | Excipient to make up to 500 g | |

The constituents are mixed, placed in capsules and the capsules then sealed. Each capsule contains 500 mg of mixture corresponding to 100 mg of sobrerol and 250 mg of tetracycline HCl.

| (2) | Sterile flask + solvent phials | | |
|---|---|---|---|
| (a) | Sterile flasks: | Tetracycline phosphate complex, equivalent to tetracycline HCl | 250 g |
| | | Magnesium chloride | 46 g |
| | | Ascorbic acid | 50 g |
| | | Lydocaine HCl | 40 g |

The powder, sterilised in a gas autoclave, is made up in small flasks with a perferatable plug, each containing 386 mg of the mixture. Each flask contains complex tetracycline phosphate equivalent to 250 mg of tetracycline HCl.

| (b) Solvent phial: | Sobrerol-d,1 | 60 g |
|---|---|---|
| | Double distilled water to make up to 3000 ml | |

The sobrerol-d,l was dissolved in double distilled water at 60° C. The rebiation was cooled, filtered, the volume was adjusted and it was placed in phials. The phials were subsequently sterilized in an autoclave at 120° C. for 30 minutes.

EXAMPLE X

Bronchodilatatory Compositions

| (1) Aerosol: | Sobrerol-d,l | 15 g |
|---|---|---|
| | Isoproterenol bitarbiate | 7.5 g |
| | Sodium methabisulphite | 2.0 g |
| | Methyl parahydroxibenzoate | 1.5 g |
| | Distilled water to make up to 1000 ml | |

The sobrerol and the methyl parahydroxybenzoate were dissolved in hot distilled water, then cooled and the sodium metabisulphite and the isoproteranol while stirring were added. The volume was adjsted and the solution was filtered. Solution was placed in dark bottles. Each ml of solution contained 15 mg of sobrerol and 7.5 mg of isoproteranol bitartrate.

In general the pharmaceutical compositions of this invention can contain any carrier which facilitates its pharmaceutical use as a liquid, a powder, a tablet, an aerosol, etc. These carriers are well known in this art.

The foregoing Examples have shown that the uniquely purified sobrerol-d,l of this invention is compatible with a great variety of therapeutic agents, or medicaments, heretofore used for therapeutic purposes in the treatment of a variety of ailments including antipyretic, analeptic, antitussive, antibiotic, and bronochodilatatory agents. Also, it has been shown that sobrerol d,l can be used in a variety of physical forms including tablets, solutions and syrups. Likewise, a variety of dosage units are disclosed, including tablets, phials and suppositories. Due to the substantial absence of toxic indications of the sobrerols-d,l hereof as demonstrated herein both pharmacologically and clinically, the highly purified sobrerol-d,l hereof (which is free, or substantially free of combined or adherent human irritants) the sobrerol-d,l hereof can be administered in a variety of ways, such as orally, topically and parenterally, as shown herein, and in a variety of dosage units as also shown herein. For instance, the Examples herein show parenteral and oral dosages varying from about 60 to 500 mg and liquids which may be used in desired quantities in concentrations varying from about 8 to 20 mg of sobrerol-d,l per ml.

It has been emphasized that it is not only necessary to have high purity sobrerol-d,l, i.e. completely racemic sobrerol, of at least 98% purity, but this high purity sobrerol-d,l must be free of irritants, especially human irritants, such as aldehydes. It has been observed, for instance, that campholene aldehyde is strongly irritating to humans and other animals, and greatly impairs the usefulness of even pure sobrerol-d,l as a medicament. Thus, therapeutically acceptable sobrerol-d,l must be substantially free of this irritant. Also, non-irritant substances such as carveols, typically produced in the production of sobrerol, reduces the activity of sobrerol-d,l as a medicament. Hence, it is important that the present process not only produce sobrerol-d,l in at least 98% purity, but also produce a sobrerol-d,l free, or substantially free, of products or by-products which are irritants or which adversely affect the therapeutic functioning of the sobrerol. The process of this invention produces sobrerol-d,l of at least 98% purity which is free of human irritants.

What is claimed is:

1. A process for treating a patient with a respiratory disease which comprises treating the patient with high purity sobrerol-d,l substantially free of human irritants, including ketones and aldehydes, in a balsamic fluidizer and expectorant and respiratory analeptic amount, said sobrerol-d,l being produced by in a first stage, epoxidizing α-pinene with a 15–30% solution of perbenzoic acid in chloroform at a temperature between $-1°$ C. and $-10°$ C. to obtain α-pinene epoxide in a second stage, forming sobrerol-d,l by hydrating said pinene epoxide at $36°$–$100°$ C. and then at an ultimate temperature between about $72°$–$100°$ C. in an aqueous solution of carbon dioxide having a ratio of about 55–100 parts by weight of α-pinene epoxide for 100 parts by weight of aqueous $CO_2$ solution, said solution having a pH of 3.5–3.9;

washing the formed sobrerol-d,l with a solvent for adhering aldehyde and ketone impurities until free of ketone and aldehyde impurities, and then drying the formed at least 98% pure sobrerol-d,l under conditions which prevent sublimation of the product to thereby produce a sobrerol-d,l free of aldehyde and ketone impurities suitable for therapeutic applications and having a melting point of $130°$–$131.5°$ C.

2. The process of claim 1, wherein in said first stage, said epoxidizing is carried out for 4–8 hours to obtain α-pinene epoxide in a yield of 80–90% of the theoretical yield and subsequently purifying said solution to obtain α-pinene epoxide having a purity of 97–98%.

3. A pharmaceutical composition containing a balsamic fluidizer and expectorant and respiratory analeptic amount of high purity sobrerol-d,l free of aldehydes and ketones, and conventional additives, excipients, carriers and solvents, said sobrerol-d,l being produced from α-pinene epoxide of 97–98% purity by hydrating said α-pinene epoxide at a temperature of about $36°$–$100°$ C. and then at an ultimate temperature between about $72°$–$100°$ C. in an aqueous solution of carbon dioxide having a ratio of about 55–100 parts of α-pinene epoxide per 100 parts by weight of aqueous $CO_2$ solution, said solution having a pH value of 3.5–3.9, washing the formed sobrerol-d,l with a solvent for the adhering aldehyde and ketone impurities until free of ketone and aldehyde impurities, and then drying the formed at least 98% pure sobrerol-d,l under conditions which prevent sublimation of the product to thereby produce a crystalline sobrerol-d,l free of aldehyde and ketone impurities suitable for therapeutic applications and having a melting point of $130°$–$131.5°$ C.

4. The pharmaceutical composition of claim 3 in the form of granules, tablets, capsules, suppositories, syrup or phial injection solutions.

5. An aqueous solution of the composition defined in claim 3.

* * * * *